United States Patent [19]

Le Floc'h et al.

[11] Patent Number: 4,918,712
[45] Date of Patent: Apr. 17, 1990

[54] DEVICE FOR DETERMINING THE MASS PER UNIT VOLUME OF AN ELEMENTARY VOLUME OF MATERIAL

[75] Inventors: Christian Le Floc'h, Blanquefort; Bernard Mazeron, St-Aubin De Medoc; Daniel Babot; Gilles Peix, both of Villeurbranne, all of France

[73] Assignee: Societe Nationale Industrielle et, Aerospatiale Societe Nationale Industrielle, Paris, France

[21] Appl. No.: 328,328

[22] Filed: Mar. 24, 1989

[30] Foreign Application Priority Data

Apr. 6, 1988 [FR] France .................................. 88 04545

[51] Int. Cl.⁴ ............................................. G01B 15/02
[52] U.S. Cl. ......................................... 378/89; 378/86
[58] Field of Search .................................... 378/89, 86

[56] References Cited

U.S. PATENT DOCUMENTS

| | | |
|---|---|---|
| 2,997,586 | 8/1961 | Scherbatskoy . |
| 3,439,166 | 4/1969 | Chope . |
| 3,505,520 | 4/1970 | Stewart et al. . |
| 3,792,252 | 2/1974 | Afanasiev et al. . |
| 4,525,854 | 6/1985 | Molbert et al. .......... 378/89 |
| 4,820,919 | 4/1989 | Berg et al. ............... 378/89 |

FOREIGN PATENT DOCUMENTS

| | | |
|---|---|---|
| 2116263 | 12/1970 | France . |
| 2582810 | 5/1986 | France . |
| 2178527 | 5/1986 | United Kingdom . |

Primary Examiner—Craig E. Church
Attorney, Agent, or Firm—Fisher, Christen & Sabol

[57] ABSTRACT

The invention provides a device for delivering an indication about the mass per unit volume of the contents of an elementary volume, comprising a directional X or gamma radiation source and a directional photoelectronic photon detector, and wherein said source and/or said detector are mounted for rotation on a common support, about an axis orthogonal to the plane defined by the axis of the radiation beam emitted by said source and by the axis of the reception channel of said detector, and means are provided for moving said common support in a direction orthogonal to the axis of rotation of said source and/or of said detector.

8 Claims, 5 Drawing Sheets

DEVICE FOR DETERMINING THE MASS PER UNIT VOLUME OF AN ELEMENTARY VOLUME OF MATERIAL

BACKGROUND OF THE INVENTION

The present invention relates to a device for determining the mass per unit volume of an elementary volume of material.

Although not exclusively, the invention is particularly adapted to the construction of a non destructive testing device for following the progression of a deposit on a wall and/or measuring a dimension or distance in an ambience where rigorous conditions prevail.

By way of particular example, the invention may be used for monitoring a zinc-lead deposit on the wall of a a zinc blast furnace.

A process is already known for obtaining an indication of the mass per unit volume of the contents of an elementary volume in which :

said elementary volume is defined as the intersection of a directional X or gamma radiation beam and a directional reception channel of a photo-electronic photon detector;

said radiation beam and/or said reception channel are made movable in rotation about an axis orthogonal to the plane defined by the axes of said radiation beam and said reception channel; and after making said intersection coincide with said elementary volume by rotation of said radiation beam and/or said reception channel, the number of photons received by said detector is measured.

Thus, as will be explained in greater detail further on, said detector receives the photons diffused by Compton effect in the direction of said detector by said radiation beam passing through said elementary volume, i.e. said detector delivers information about the number of electrons contained by said elementary volume and so about the mass per unit volume thereof.

SUMMARY OF THE INVENTION

The device of the invention, for delivering an indication about the mass per unit volume of the contents of an elementary volume, comprising a directional X or gamma ray source and a directional photo-electron photon detector, is characterized in that said source and/or said detector are mounted for rotation on a common support about an axis orthogonal to the plane defined by the axis of the radiation beam emitted by said source and by the axis of the reception channel of said detector and means are provided for moving said common support in a direction orthogonal to the axis of rotation of said source and/or of said detector.

Preferably, the device of the invention comprises in addition means for moving said support in a direction parallel to the axis of rotation of said source and/or of said detector.

Thus, with the invention, said elementary volume of material may be readily brought to any desired position, and the position of said intersection may be varied.

Consequently, by using the device of the invention, it is possible :

(a) to measure the mass per unit volume of said elementary volume, for example by comparing the electron flow delivered by the detector with the electron flow delivered by the same detector when, under the same operating conditions, the same radiation beam passes through an identical elementary volume of a standard material whose mass per unit volume is known. In fact, the number of photons diffused by Compton effect is directly proportional to the number of electrons contained in said elementary volume, this number of electrons being itself in a constant ratio with that of the nucleons of said elementary volume. Thus, the two flows compared are in the same ratio as the masses per unit volume compared.

(b) to maintain said intersection at a fixed position and measure the evolution in time of the electron flow delivered by said detector. Thus, indications are obtained about the evolution of the mass per unit volume of said elementary volume, for example as a function of the development of a chemical reaction or a physical process.

(c) to move said intersection and, for a plurality of positions of said intersection, to measure the corresponding electron flows delivered by said detector. A veritable map of the mass per unit volume of the space in which said intersection is moved may thus be drawn up. In addition, when, during such movement, the electron flow varies suddenly, that means that we pass from a dense material to a less dense material or vice versa. With such sudden variation of the electron flow it is therefore possible to determine the transition between a dense object and its gaseous environment, i.e. in actual fact to determine the position of said object. It will be noted that the movement of said intersection may be obtained either by rotation of the radiation beam and/or of the reception channel alone or by relative movement of said object with respect to said radiation beam and said reception channel alone, or else a combination of the two.

To simplify the mechanical assembly of the source, of the detector and/or of their support, while having the maximum examination possibilities, or else for increasing the speed and/or accuracy of the measurement, the device may comprise a plurality of directional photo-electronic detectors. At a given time, these detectors may converge towards the same point of a single radiation beam emitted by said source, or towards different points thereof. Furthermore, said source may emit several radiation beams and a detector may be associated with each radiation beam.

In an advantageous embodiment, the active element of the radiation source (X-ray tube, radioactive material, ...) and that of the detector (scintillator) are enclosed in a solid screen comprising a narrow duct forming a collimator connecting said active element to the outside of said screen. It is these narrow ducts which determine the section of the directional radiation beam and that of the directional reception channel and so the elementary volume of material examined.

In the applications envisaged for the device of the invention, such solid screens may be made from lead, when the temperature conditions of the ambient medium are normal, or else from impoverished uranium, tungsten, ... when the temperature conditions imposed on said screens are high.

Closure means may be provided for the ducts of the screens so as to isolate said active elements outside periods of measurement.

If the device of the invention is used in ambient conditions in which different particles (dust, materials in suspension likely to be deposited, ...) are found, blowing of the orifices of said ducts may be provided so as to prevent clogging thereof and/or jamming of said closure means.

BRIEF DESCRIPTION OF THE DRAWINGS

The figures of the accompanying drawings will better show how the invention may be implemented. In these figures identical references designate similar elements.

DESCRIPTION OF THE PREFERRED EMBODIMENTS

Figures 1, 2, 3:
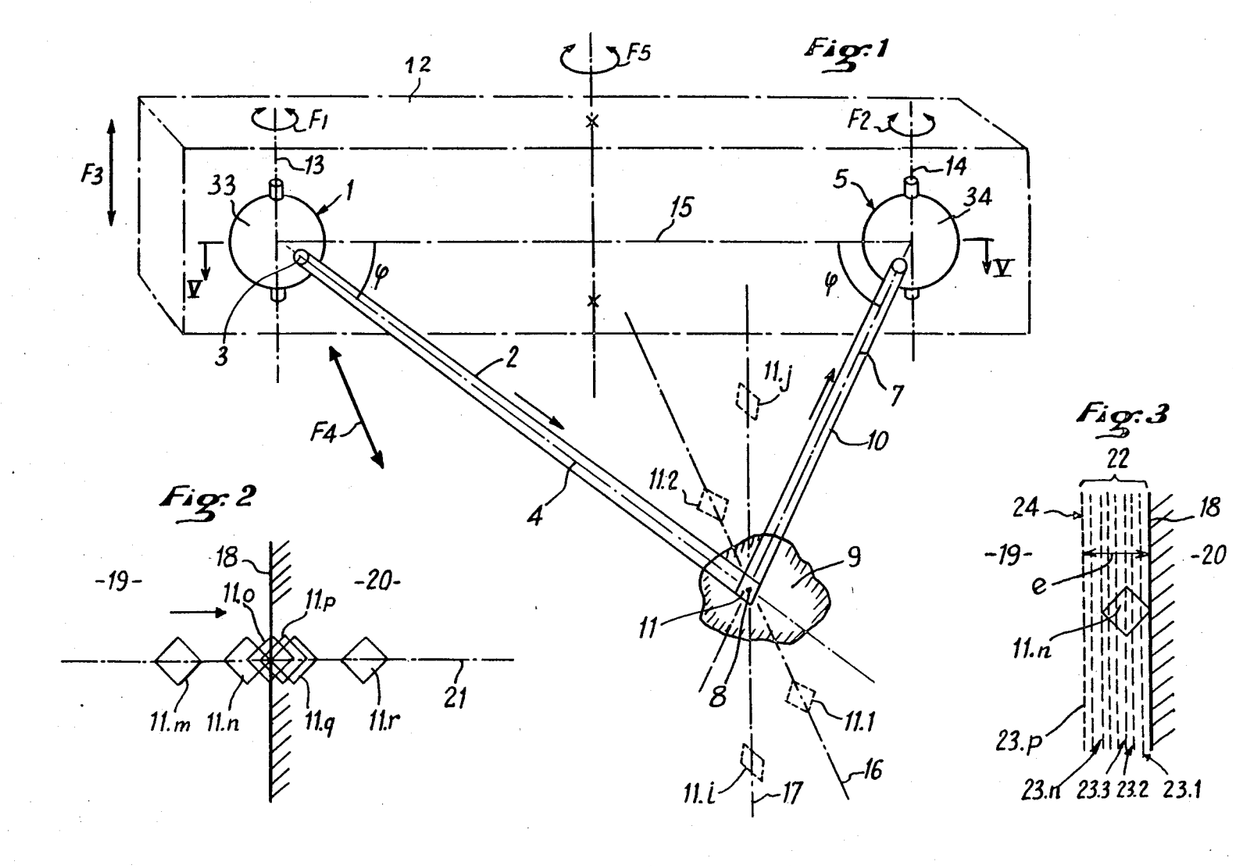
FIG. 1 illustrates schematically, in perspective, the device of the present invention.
FIGS. 2, 3 and 4 illustrate schematically and respectively three applications of the present invention.

The device of the invention, shown schematically in FIG. 1, comprises an X or gamma radiation source 1 emitting a directional beam 2 of such radiation through its emission window (collimator) 3 with axis 4, and a directional photon detector 5 having a reception window 6 (collimator) with axis 7. Said source 1 and/or said detector 5 are movably mounted, for example in the way described hereafter, so that their axes 4 and 7 may be brought to converge at a point 8 of desired position. In FIG. 1, it is assumed that this convergence point 8 was inside a volume of material 9.

When the directional beam 2 penetrates into the volume of material 9, its photons impact the electrons of said material and, by Compton effect, lower energy photons are diffused in all directions. Since the reception window 6 is directed towards point 8, detector 5 is capable of receiving those of these photons diffused by Compton effect which have a direction of propagation parallel to axis 7 and which are inside a virtual reception channel 10, formed by the cylindrical surface whose directrix is the contour of the reception window 6 and whose generatrix is parallel to axis 7. Of course, the contour of the reception window 6 is not necessarily circular, so that the term "cylindrical surface" must be understood in its mathematical meaning, which includes surfaces whose directrix may be a line of different forms, and particularly polygonal (and even more especially rectangular or square).

Thus, detector 5 receives and counts all the photons diffused in the reception channel 10 and which come from an elementary volume 11 of material, defined by the intersection of the radiation beam 2 and the reception channel 10.

The number of photons measured by detector 5 is therefore proportional to the number of electrons contained in said elementary volume 11 and, since in all the elements (except hydrogen) the number of electrons is in a ratio close to 0.5 with the number of nucleons, the number of photons counted by detector 5 is representative of the mass per unit volume of said elementary volume 11. Of course, for this it is indispensable that between the elementary volume 11 and the reception window 6 no parasite diffusion of photons occurs in the reception channel 10, which is the case if the elementary volume 11 is on the surface and if the reception channel passes through a gas, for example air.

Thus, with the present invention, a non destructive and contactless measurement may be be made of the mass per unit volume of the material of the elementary volume 11 (called hereafter measurement volume), which may be positioned at any point in the volume of material 9, through the mobility of the radiation source 1 and of the photon detector 5.

For this, said radiation source 1 and said photon detector 5 could be made movable independently of each other, in any desired way, the only requirement being that axes 4 and 7 may be caused to converge at a point 8.

However, in the advantageous embodiment of the present invention, the radiation source 1 and the photon detector 5 form an integral assembly 12, inside which said source 1 and said detector are mounted for rotation (see arrows F1 and F2) about respective and parallel axes 13 and 14, said axes of rotation 13 and 14 being orthogonal to the plane defined by the axis 4 of source 1 and by the axis 7 of detector 5. To simplify location of the elementary measurement volume 11, the spacing (symbolized by the dash dot line in FIG. 1) between said source 1 and said detector 5 is kept constant and, in addition, the rotations thereof about the respective axes of rotation 13 and 14 are coupled so that the inclination angles 0 of axes 4 and 7 in the plane which they define are symmetrical. Finally, the integral assembly 12 may be adapted to be moved, as a whole, parallel to the axes of rotation 13 and 14 (see arrow F3) and/or orthogonally to the plane defined by said axes of rotation 13 and 14 (see arrow F4).

Thus, for a given position of the integral assembly 12, if source 1 and detector 5 are caused to rotate respectively about said axes of rotation 13 and 14, the elementary volume 11 assumes different positions 11.1, 11.2, aligned with the bisector 16 of the angle formed by axes 4 and 7. It will be noted that, if the angles of inclination 0 of axes 4 and 7 are kept constant and if the integral assembly 12 is moved orthogonally to the axes of rotation 13 and 14 (arrow F5), said elementary measurement volume 11 moves similarly along bisector 16 and may assume said positions 11.1, 11.2.

Finally, when the angles of inclination 0 of axes 4 and 7 are kept constant and when the unit assembly 12 is moved parallel to the axes of rotation 13 and 14 (arrow F4), the elementary measurement volume 11 moves along a line 17 parallel to said axes of rotation 13 and 14, and takes different positions 11.i, 11.j.

It can then be seen that, by combining the above described movements (or some of them), it is possible to position the elementary measurement volume 11 in any desired position.

In FIG. 2, a first application of the invention has been shown. A wall 18 has been shown separating two media 19 and 20 having very different mass per unit volumes. For example, medium 19 is not very dense and is formed by a gas such as air, while medium 20 is a dense solid, i.e. comprising a high electron density. In addition, it is assumed that the elementary measurement volume 11 is moved along a line 21 (which is for example line 16 or line 17 or a combination of the two), to pass from medium 19 to medium 20 (or conversely) by passing through wall 18. When the elementary measurement volume 11 is situated in medium 19, in a position 11.*m* spaced apart from wall 18, the number of diffused photons counted by the detector is low. This low number of diffused photons remains substantially constant until the elementary measurement volume 11 reaches a position 11.*n* in which it is just in contact with wall 18. With further movement of the elementary measurement volume 11, an increasing portion thereof passes through wall 18 (see positions 11.*o* and 11.*p*) and penetrates into the dense medium 20, so that the diffused photons counted by detector 5 increases. When the elementary measurement volume 11 reaches position 11.*q*, it is completely inside the dense medium 20, so that the number of diffused photons counted by detector 5 is high. This number remains substantially constant if the elementary measurement volume 11 takes up a position 11.*r*, spaced away from wall 18, but close thereto.

To explain the phenomenon, a relatively large measurement volume 11 has been shown schematically in FIG. 2. In actual fact, since this elementary measurement volume 11 results from the intersection of the collimated radiation beam 2 and of the reception channel 10 also collimated, it is very small and the transition between positions 11.*n* and 11.*q* (in which this elementary measurement volume 11 is adjacent wall 18 but on each side thereof) is very rapid. Consequently, the number of diffused photons counted by detector 5 passes practically without transition from a low (or zero) value to a high value. Of course, if the movement took place reciprocally from medium 20 to medium 19, the number of said photons would pass practically instantaneously from a high value to a low value.

Consequently, the sudden change of value of the number of diffused photons counted by detector 5 is characteristic of crossing the separation wall 18. It is then possible to detect the position thereof. In addition, by locating the position of the integral assembly 12 and/or the value of the inclination angles 0 of axes 4 and 7 corresponding to the sudden change of value of the number of diffused photons counted by detector 5, the distance of the separation wall 18 from an initial position may be measured.

FIG. 3 illustrates a second application of the invention. In this figure, we find again the two preceding media 19 and 20 separated by a wall 18. In this case, it is assumed that a deposit 22 of dense material is likely to form progressively, thin layer by thin layer, on said wall 18 on the side of the less dense medium 19 and it is desired to follow the evolution of this deposit in time. For this, the elementary measurement volume 11 is brought into the position 11.*n*, in which it is adjacent wall 18, on the side of the lesser dense medium 19 and is kept in this position throughout the whole measurement.

Initially, i.e. before formation of the deposit 22 begins, the elementary measurement volume 11 is surrounded by the lesser dense medium 19, so that the number of diffused photons given by detector 5 is very low, if not zero. When a first thin layer 23.1 of deposit 22 is formed, a part of the elementary measurement volume 11 is filled thereby, so that the number of diffused photons counted by detector 5 increases. As the formation of the thin successive layers 23.1, 23.2, 23.3, . . . 23.*n* of the dense deposit 22 takes place progressively, the number of diffused photons continues to increase. Consequently, the variation of said number of photons makes it possible to follow the evolution of the formation of layers 23.*i* of deposit 22. When the elementary measurement volume 11 is completely filled by deposit 22 (layer 23.*n*) and when additional deposition layers 23.*p* continue to form, these additional layers 23.*p* cause attenuation of the incident radiation beam 2 and of the beam of photons diffused along the reception channel 10. Consequently, the number of diffused photons counted by detector 5 decreases. Thus, during the measurement, this number of counted photons increases, passes through a maximum then decreases.

The rate of increase and decrease of said number of counted photons is representative of the speed of formation of deposit 22 and of its density.

Of course, if it is desired to know the position of the free surface 24 of deposit 22 in medium 19, the operation may be as described in connection with FIG. 2. The movement of the elementary measurement volume 11 is then representative of the thickness e of deposit 22.

In the two applications described above in connection with FIGS. 2 and 3, circumstances occur in which the elementary measurement volume 11 is partially or totally empty of dense material 20, since it is situated wholly or partially in the lesser dense medium 19. It is advantageous for the latter to be chosen (gas such as air for example) so that the number of photons counted by detector 5 is proportional to the proportion of dense medium 20 filling the elementary volume of material, i.e. said less dense material 19 causes diffusion of photons which may be considered as zero. Thus, the theoretical sensitivity of the device of the invention depends solely on geometrical conditions. It will be noted that, in addition, such sensitivity is independent of the radiation energy of beam 2.

Figure 4:
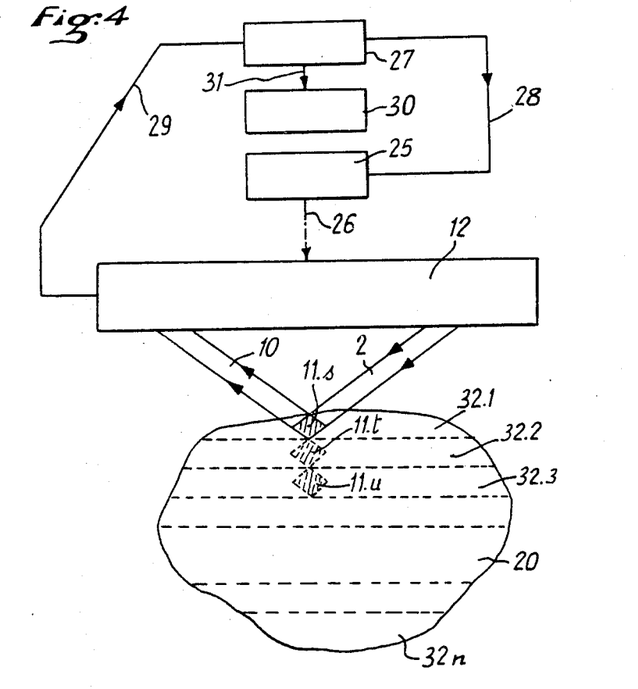

In the application illustrated in FIG. 4, the invention is used for measuring the mass per unit volume of a volume of dense material 20. In this figure, a robot 25 has been provided for moving the integral assembly 12 and/or orienting source 1 and detector 5 (connection 26). Robot 25 is controlled by a microprocessor 27 ((connection 28) which receives the counting information from detector 5 (connection 29). A device for processing the data and results 30 receives the information from microprocessor 27 (connection 31). In this case, the operation is carried out slice by slice.

A surface slice 32.1 is first of all examined by placing the elementary measurement volume 11 there, which then takes the position 11.*s*, and the mass per unit volume of volume 11.*s* is determined, for example by reference to the mass per unit volume of a standard material previously put in place of the dense material 20 and examined under the same conditions. If we consider the surface slice 32.1 is homogeneous, we now know the mass per unit volume thereof at any position. If not, said surface slice 32.1 is examined point by point by moving the elementary measurement volume 11. We then pass to examination of the underlying slice 32.2. The result of measuring this underlying slice 32.2 will depend not only on the mass per unit volume to the measurement volume 11.*t*, but also on the attenuation undergone by the photons which pass through the first slice 32.1 not only for the incident beam 2 but also along the diffused beam 10. Such attenuation of course falsifies the result of the measurement, but since the mass per unit volume of the medium is already known at all points of the first slice, it is possible to take it into account during examination of the second slice and correct the result. Thus, the mass per unit volume of mass 20 is obtained at all points of slice 32.2. It is then possible to pass to examination of a third slice, while taking into account the attenuation through the first two, etc . . .

Generally, calculation shows that the measurement of the number of photons diffused by a slice $32.j$ is related to the measurement of the number of photons diffused by the preceding slice $32.i$ by a recurrence formula involving the thickness of said slices, the angle of incidence of beam 2 and the equivalent linear absorption coefficient of said slice $32.j$. Therefore said equivalent linear absorption coefficient may be determined and, from it, the mass per unit volume of the slice $32.j$ concerned.

In this case of application, computer 27 is indispensable for storing the results and making the necessary calculations.

Figure 5:
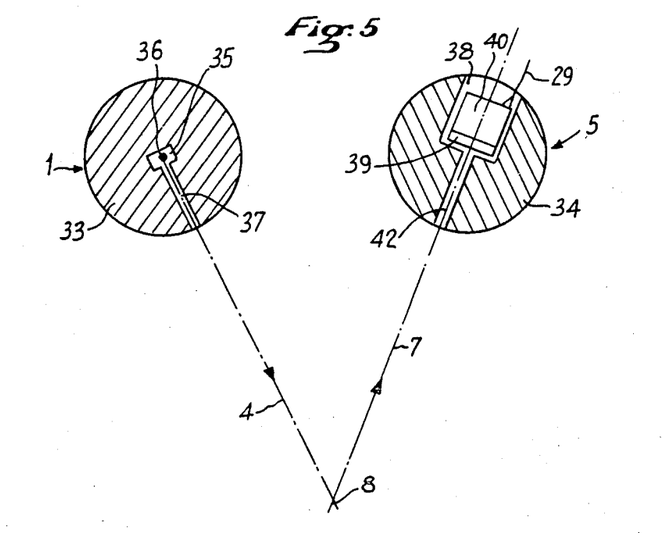
FIG. 5 shows schematically one embodiment of the source and detector of the device of FIG. 1, in section through line V—V of this latter figure.

In the embodiment of source 1 and detector 5 given by way of example and shown schematically in FIG. 5, spherical screens 33 and 34 have been provided for each of them. It is these screens which are mounted for rotation about axes of rotation 13 and 14. The screens are formed of solid spheres, for example made from impoverished uranium, tungsten, doped ceramic material, etc . . . so as to withstand high temperatures (application to blast furnaces), while having a large efficient section for capturing the photons. If required, a system for cooling said screens may be provided, for example by fluid flow. In the case where, in the application envisaged, screens 33 and 34 are not subjected to high temperatures, they may be made from lead or from a doped composite material.

The spherical screen 33 comprises a central recess 35, inside which the active X or gamma ray generating element 36 is disposed. This active element may for example be an X-ray tube, having a very stable high voltage and high output, so as to reduce statistical uncertainties. The active element 36 may also be a high output radioactive source of adequate period, such for example as a cobalt 60 source. The central recess 35 communicates with the outside through a narrow duct 37 whose axis merges with axis 4, this duct 37 playing the role of collimator defining radiation beam 2.

The spherical screen 34 of detector 5 comprises a recess 38 for housing the active reception element. This is formed for example of a scintillator 39, for example made from sodium iodide doped with thallium, with which a photomultiplier 40 is associated for collecting the photons therefrom and transforming them into electric pulses. The electric pulses output by the photomultiplier are fed over a connection 41 to an electronic acquisition and processing chain of a type known by a man skilled in the art and not shown. Scintillator 39 receives the photons through a narrow duct 42, whose axis merges with axis 7 and which serves as collimator for determining the section of the reception channel 10.

The narrow ducts 37, 42, which define respectively beam 2 and reception channel 10, define the elementary measurement volume 11, which is the intersection thereof. The spherical screens 33 and 34 stop the parasite photons which do not follow the guiding imposed by ducts 37, 42. The background noise of the device of the invention is therefore low.

Figure 6:
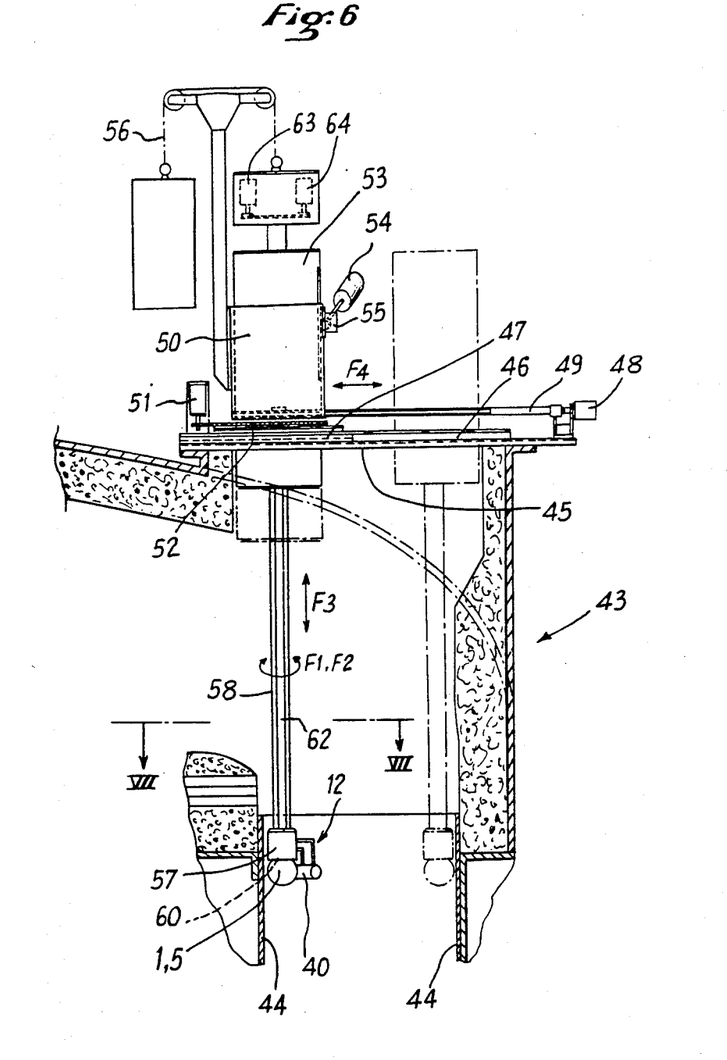
FIG. 6 shows, in partial schematic section, a blast furnace in which a device of the present invention is installed.
Figures 7, 8:
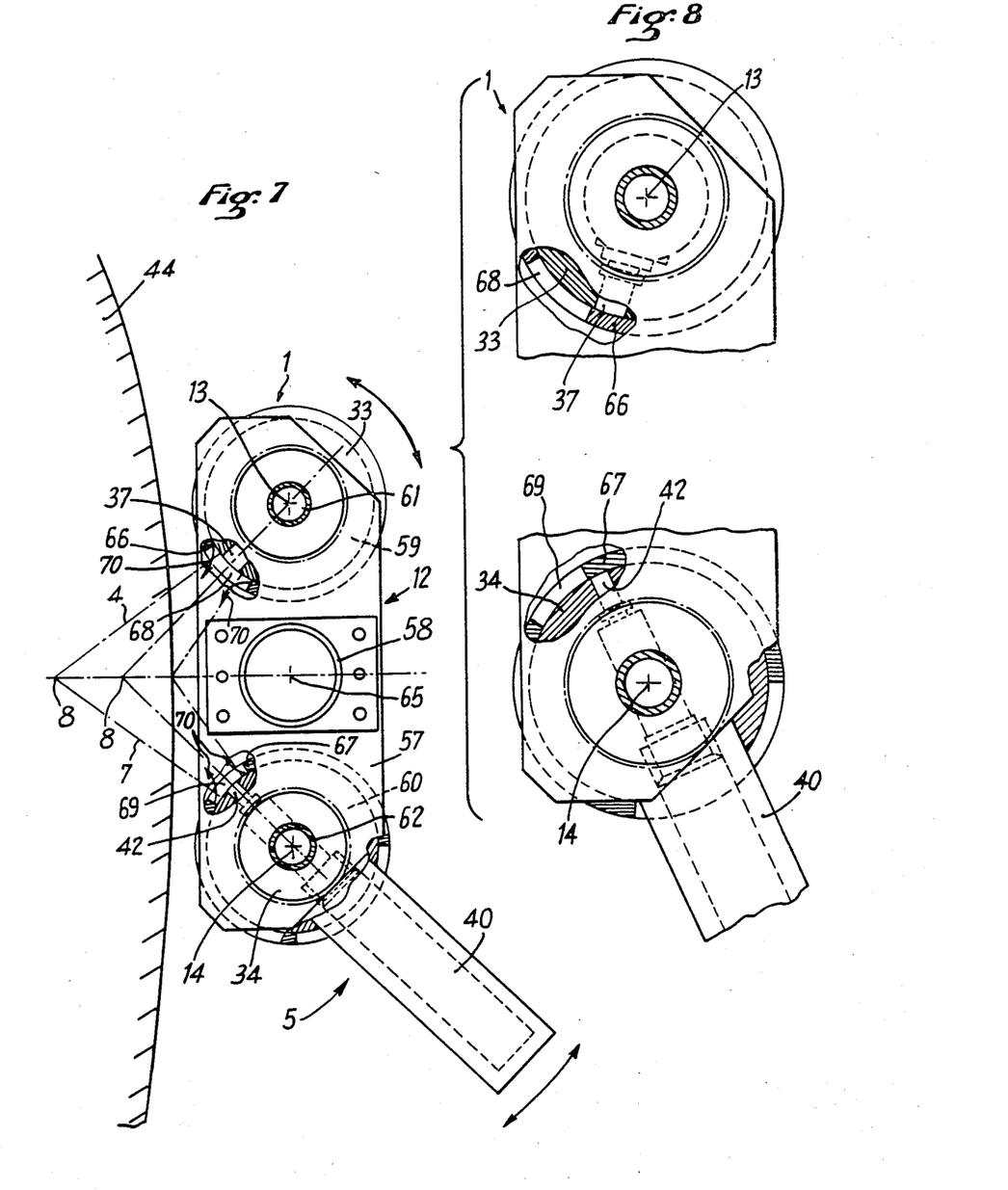
FIG. 7 is a section, on a larger scale, corresponding to line VII—VII of FIG. 6 and illustrating one embodiment of the source-detector assembly.
FIG. 8 illustrates, in a view similar to FIG. 7, the source and the detector in the closed position.

It will be noted, as will be shown more particularly with reference to FIGS. 6 and 7, that the spherical shape of screens 33 and 34 is advantageous for obtaining the degrees of freedom which are necessary for them.

In FIG. 6, a zinc blast furnace 43 has been shown, partially in vertical section, in which it is desired to monitor the evolution of the zinc-lead deposit on a wall 44, for example cylindrical. The device shown is mounted through an opening 45 in the blast furnace 43. It comprises :

guide rails 46 fixed to said blast furnace 43, a carriage 47 slidable along guide rails 46, under the action of a motor 48 and a transmission 49, a sleeve 50 mounted for rotation about a vertical axis on said carriage 47, the orientation of said sleeve 50 being controlled by a motor 51 and a transmission 52.

a core 53 slidable vertically inside sleeve 50 under the action of a motor 54 and a transmission 55, said integral assembly 12 being suspended from said core 53 so as to be situated opposite the wall 44 to be monitored; and a counterweight balancing assembly 56 for balancing core 53 and the integral assembly 12.

As shown in FIG. 7, this integral assembly 12 comprises a common support 57 for source 1 and detector 5 and is suspended from core 53 by means of a column 58. Support 57 comprises spherical impressions 59, 60 respectively for serving as hub with vertical axis for spheres 33 and 34 of source 1 and detector 5. Said spheres 33 and 34 are respectively fast with vertical shafts 61, 62 (with respective axes 13 and 14) connected to motors 63, 64 mounted on said core 53.

Thus, through motors 63, 64 and shafts 61, 62, source 1 and detector 5 may rotate about their respective axes of rotation 13 and 14 (arrows F1 and F2);

through motor 54 and transmission 55, the integral assembly 12 may be moved vertically in translation (arrow 3); and through motor 48 and transmission 49, the integral assembly 12 may be moved horizontally (arrow 4).

Wall 44 may therefore be examined by the device of the invention using one of more of the above described methods, particularly in connection with FIGS. 2 and 3.

It will be further noted that, through motor 51 and transmission 52, the integral assembly 12 may rotate as a whole about the axis 65 of column 58, this axis 65 being parallel to axes of rotation 13 and 14 (see arrow F5 in FIG. 1).

As shown in FIGS. 7 and 8, each sphere 33 and 34 of source 1 and detector 5 is associated with a screened casing 66 or 67, in which an opening 68 or 69 is formed for beam 4 or the reception channel 10. Thus, by a relative movement of sphere 33 (or 34) and the associated screened casing 66 (or 67) it is possible to close off collimators 37 and 42 of source 1 and receiver 5, either for transport or outside a measurement period. In FIG. 7, a measurement phase has been illustrated, collimators 37 and 42 being opposite the respective openings 68 and 69. On the other hand, in FIG. 8, the device is at rest, collimators 37 and 42 being shut off by the screened casings 66 and 67.

It may be advantageous to provide compressed air jets (shown schematically in FIG. 7 by arrows 70) for licking openings 68 and 69 so as to prevent the formation of any deposit which could disturb the measurement, or prevent the relative movement of spheres 33, 34 and casings 66, 67.

Figure 9:
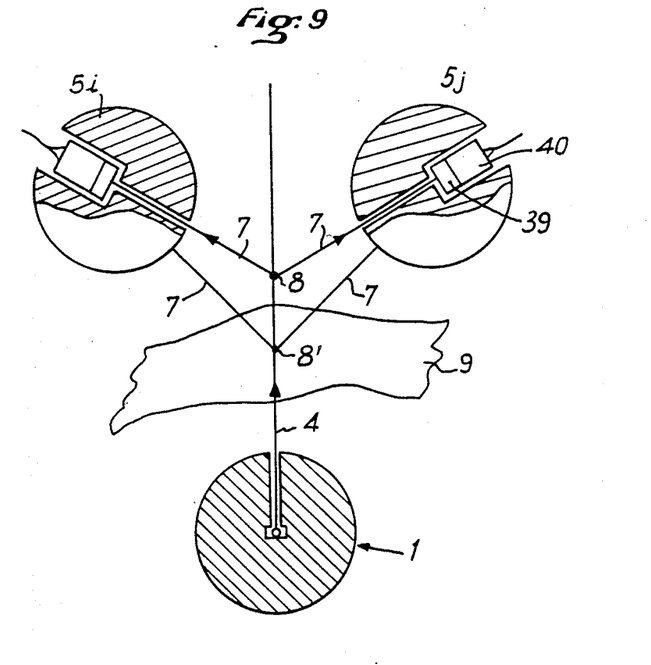
FIGS. 9 and 10 illustrate two variants of implementing the present invention.

In the variant of construction of the device of the invention shown in FIG. 9, a plurality of detectors $5i$, $5j$ is provided, distributed for example in a ring about the axis 4 of the radiation beam emitted by source 1. Detectors $5i$, $5j$ are orientable individually and/or together. Thus, they may be all oriented simultaneously towards the same point 8, which increases the accuracy of the measurement (and in this case they are connected preferably to the same counting chain), or else be oriented simultaneously towards different points 8, 8', . . . of axis 4. In the latter case, measurement of the mass per unit volume along axis 4 may be carried out in a single operation.

Figure 10:
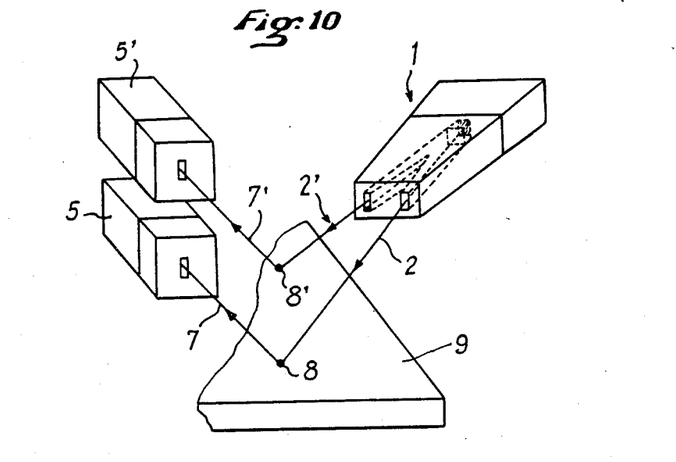

As shown in FIG. 10, source 1 may also emit several radiation beams 2, 2' (e.g. by adequate collimation) and with each of these beams may be associated a detector 5, 5'. In this case also, the mass per unit volume of a material 9 may be measured simultaneously at different points 8, 8' thereof.

What is claimed is:

1. Device for delivering an indication about the mass per unit volume of the contents of an elementary volume comprising:
   a movable common support (12, 57);
   a directional X or gamma radiation source (1) rotatively mounted on said common support about a first axis (13);
   a directional photoelectronic photon detector (5) rotatively mounted on said common support about a second axis (14);
   said first and second axes being orthogonal to the plane defined by the axis (4) of the radiation beam (2) emitted by said source (1) and by the axis (7) of the reception channel (10) of said detector (5);
   means (63, 64) for rotating said source (1) and said detector (5) about said first and second axes, respectively; and
   means (46, 47, 48, 49) for moving said common support in a direction orthogonal to said first and second axes.

2. The device as claimed in claim 1 further comprising means for moving said support in a direction parallel to the axis of rotation of said source and/or of said detector.

3. The device as claimed in claim 1 comprising further means (50, 51, 52) for rotating said movable common support about an axis (65), parallel to said first and second axes.

4. The device as claimed in claim 1 wherein the active element of said detector is fitted inside a solid screen comprising a narrow duct forming a collimator and connecting said active element to the outside of the screen.

5. The device as claimed in claim 1 wherein said detector is a plurality of directional photoelectronic detectors which are mounted for rotation on said common support.

6. The device as claimed in claim 5 wherein said source emits a plurality of radiation beams and each of said detectors is associated with one of said beams.

7. The device as claimed in claim 1 wherein the active element of said radiation source is fitted inside a solid screen comprising a narrow duct forming a collimator and connecting said active element to the outside of the screen.

8. The device as claimed in claim 7 or 4 wherein said solid screen has a spherical shape.

* * * * *